United States Patent
Bundela et al.

(10) Patent No.: US 10,140,341 B2
(45) Date of Patent: Nov. 27, 2018

(54) METHODS FOR DRUG REPURPOSING AND DEVICES THEREOF

(71) Applicant: Infosys Limited, Bangalore (IN)

(72) Inventors: Saurabh Bundela, Chhatarpur (IN); Krutin Kumar Boloor, Bangalore (IN); Pooja Durgad, Davangere (IN); Rajesh Lawrence Patrao, Mangalore (IN); Deepak Pn, Bangalore (IN)

(73) Assignee: Infosys Limited, Bangalore (IN)

( * ) Notice: Subject to any disclaimer, the term of this patent is extended or adjusted under 35 U.S.C. 154(b) by 607 days.

(21) Appl. No.: 14/612,642

(22) Filed: Feb. 3, 2015

(65) Prior Publication Data

US 2015/0227700 A1    Aug. 13, 2015

(30) Foreign Application Priority Data

Feb. 13, 2014   (IN) .............................. 676/CHE/2014

(51) Int. Cl.
*G06F 17/30*   (2006.01)
*G06F 19/00*   (2018.01)

(52) U.S. Cl.
CPC .......... *G06F 17/3053* (2013.01); *G06F 19/70* (2013.01)

(58) Field of Classification Search
CPC ...... G06F 17/3053; G06F 19/70; G06F 19/12; G06F 19/16; G06F 19/3443; G06F 19/704; G06F 19/705; G06F 19/326; G06F 19/34; G06F 19/3437; G01N 33/5008; G01N 33/502; G01N 33/5041
USPC ........................................................ 707/730
See application file for complete search history.

(56) References Cited

U.S. PATENT DOCUMENTS

| | | |
|---|---|---|
| 6,859,735 B1 | 2/2005 | Stoughton et al. |
| 7,660,709 B2 | 2/2010 | Bugrim et al. |
| 2008/0161228 A1* | 7/2008 | Ryals ................. G01N 33/5008 702/19 |
| 2010/0161301 A1* | 6/2010 | Arakelyan ............ G06F 19/704 703/11 |
| 2012/0011156 A1* | 1/2012 | Chen ....................... G06F 19/12 707/776 |
| 2013/0138478 A1* | 5/2013 | Hyde ................. G06Q 30/0204 705/7.33 |
| 2014/0193517 A1* | 7/2014 | Agarwal ............. G06F 19/3437 424/600 |
| 2016/0171173 A1* | 6/2016 | Xie ......................... G06F 17/30 705/2 |

* cited by examiner

*Primary Examiner* — Evan Aspinwall
(74) *Attorney, Agent, or Firm* — LeClairRyan PLLC

(57) ABSTRACT

The present invention provides a method and system for drug repurposing. In accordance with a disclosed embodiment, the method may include selecting a set of positive drugs for an indication and listing a set of pathways for the set of positive drugs and a set of negative drugs. Further, the method shall include associating a pathway for each drug with an index value, based on an action of the each drug on the pathway. A pathway weight shall be calculated from the index value of the each pathway based on a frequency of occurrence of the each pathway in the set of positive drugs and in the set of negative drugs. A drug score for a drug to be repurposed shall be identified from the negative set of drugs, based on the pathway weight. The drug with a relatively high drug score can be repurposed for the indication.

21 Claims, 4 Drawing Sheets

METHODS FOR DRUG REPURPOSING AND DEVICES THEREOF

This application claims the benefit of Indian Patent Application Serial No. 676/CHE/2014 filed Feb. 13, 2014, which is hereby incorporated by reference in its entirety.

FIELD

The present invention relates generally to a method and system for drug repurposing. More specifically, the present invention relates to a method and system for identifying approved drugs for cure of new therapeutic indications.

BACKGROUND

Drug repurposing is a strategy by which new or additional value is usually generated from a drug by targeting diseases other than those diseases for which the drug was originally intended. The drug repositioning strategy has been known to resolve a problem of high expenditure in discovering new remedies for diseases. Advantages of the drug repurposing include reduced research and development costs, and improved probability of success as a repositioned drug will have passed related toxicology and safety assessments.

Currently individual in-silico approaches are adapted for the drug repurposing. Certain approaches that apply a mechanism of action fail to provide an informatics view of data related to the drug, pathways and an indication to be treated. Hence there is a need for an alternate method and system that takes the informatics view of the data related to the drug, the indication, the pathway and target information for building a pathway frequency based model. This pathway frequency based model can be used for prediction of fitment of the repurposed drug for the indication.

The alternate system and method must also include a clustering approach for generation of an alternate scoring and prediction mechanism for the repurposed drugs. Thus a unique system and method for drug repurposing is proposed.

SUMMARY

The present invention provides a method and system for drug repurposing. In accordance with a disclosed embodiment, the method may include selecting a set of positive drugs for an indication and listing a set of pathways for the set of positive drugs and a set of negative drugs. Further, the method shall include associating a pathway for each drug with an index value, based on an action of the each drug on the pathway. A pathway weight shall be calculated from the index value of the each pathway based on a frequency of occurrence of the each pathway in the set of positive drugs and in the set of negative drugs. A drug score for a drug to be repurposed shall be identified from the negative set of drugs, based on the pathway weight.

In an additional embodiment, a system for drug repurposing is disclosed. The system comprises a selection unit that can select a list of positive drugs for an indication. A lookup table shall enlist a set of pathways for the set of positive drugs and a set of negative drugs. Further, an indexing unit can be configured to associate a pathway for each drug with an index value, based on an action of the each drug on the pathway. The system shall further include a calculation unit, configured to calculate a pathway weight from the index value of the each pathway based on a frequency of occurrence of the each pathway in the set of positive drugs and in the set of negative drugs; and a drug score for the each drug based on the pathway weight.

These and other features, aspects, and advantages of the present invention will be better understood with reference to the following description and claims.

While systems and methods are described herein by way of example and embodiments, those skilled in the art recognize that systems and methods proposed for drug repurposing are not limited to the embodiments or drawings described. It should be understood that the drawings and description are not intended to be limiting to the particular form disclosed. Rather, the intention is to cover all modifications, equivalents and alternatives falling within the spirit and scope of the appended claims. Any headings used herein are for organizational purposes only and are not meant to limit the scope of the description or the claims. As used herein, the word "may" is used in a permissive sense (i.e., meaning having the potential to) rather than the mandatory sense (i.e., meaning must). Similarly, the words "include", "including", and "includes" mean including, but not limited to.

DETAILED DESCRIPTION

Disclosed embodiments provide computer-implemented methods, systems, and computer-program products for repurposing a drug. More specifically the methods, and systems disclosed implement a mechanism of action approach, for accelerating the repurposing of the drug, based on a premise that drugs acting in the same indication can act similarly at mechanistic level.

Figure 1:
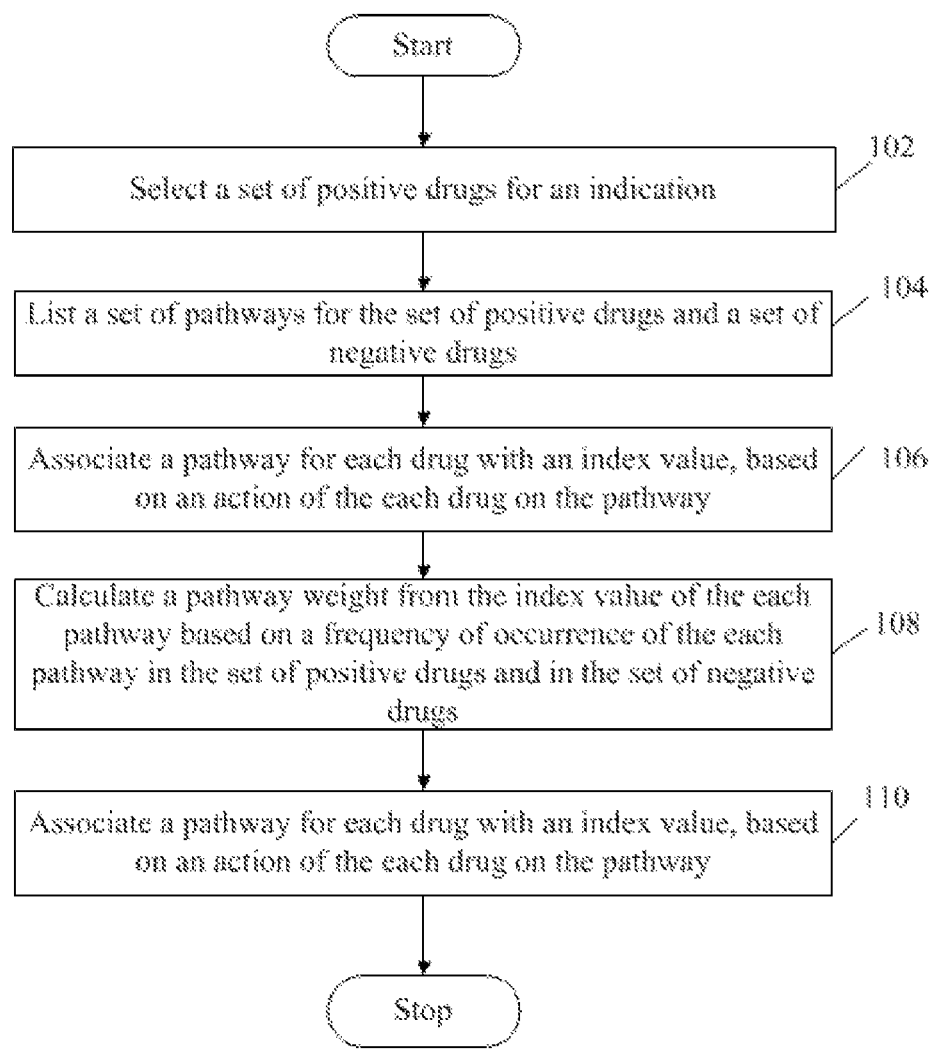
FIG. 1 is a flowchart illustrating an embodiment of a method for distributed probabilistic matrix factorization.

FIG. 1 is a flowchart that illustrates a method performed in repurposing a drug in accordance with an embodiment of the present invention. A set of positive drugs for an indication viz. drugs that are known to have a therapeutic effect on said indication, are selected at step 102. The drugs in a universal set of drugs, apart from the set of positive drugs, can be referred to as a negative set of drugs. The negative set of drugs is basically a set of drugs that are now known to have a therapeutic effect on the indication. At step 104, a set of pathways, for the set of positive drugs, and the set of negative drugs, shall be listed. At step 106, a pathway for each drug shall be associated with an index value, based on an action of the drug on the pathway. Further, at step 108, a pathway weight can be calculated from the index value of the each pathway based on a frequency of occurrence of the each pathway in the set of positive drugs and in the set of negative drugs. Finally a drug score for a drug from the negative set of drugs can be identified based on the pathway weight, at step 110. The drug score is usually an indication of whether drug may be repurposed. A higher drug score can indicate that the drug maybe repurposed for said indication.

Figure 2:
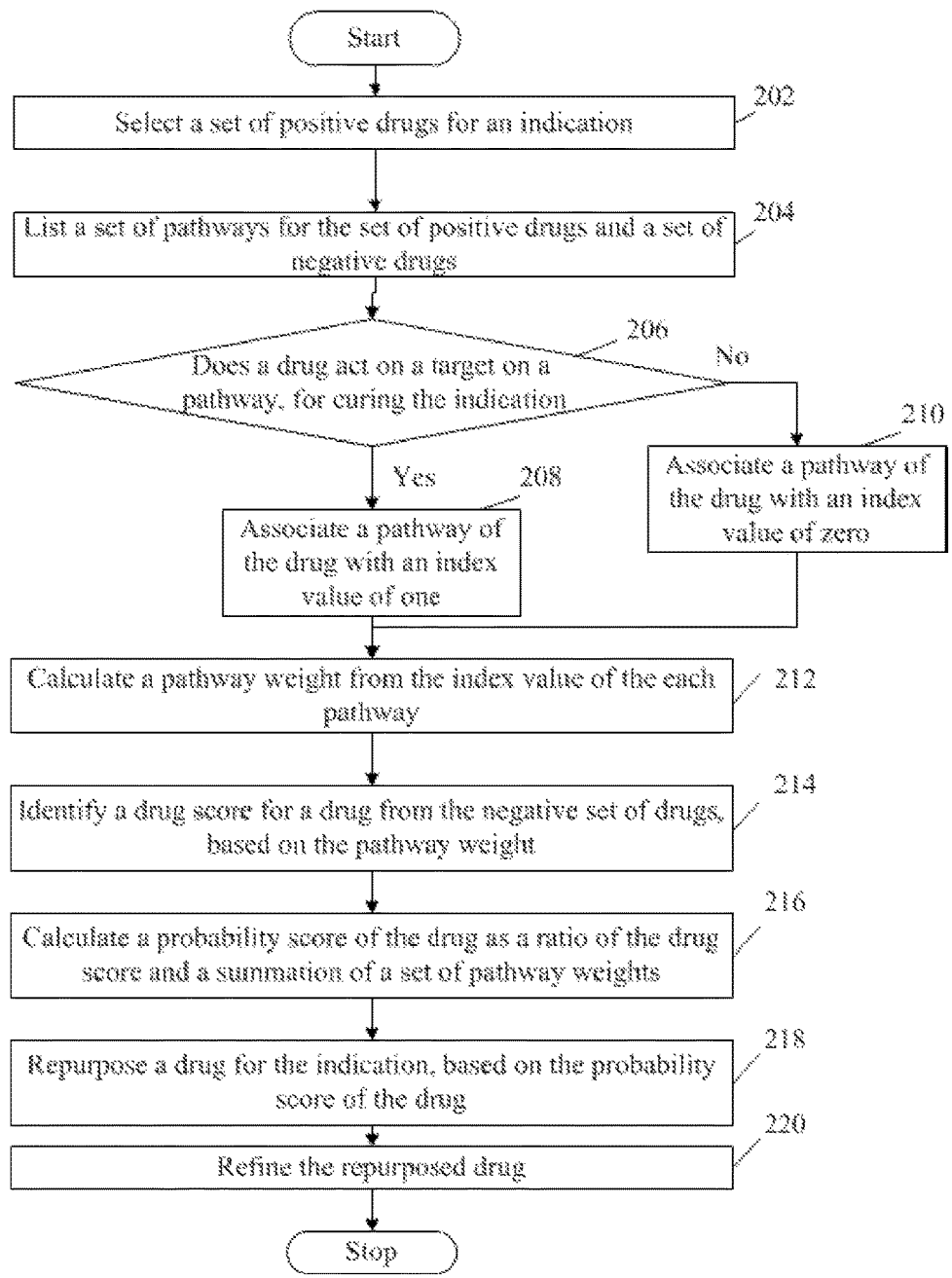
FIG. 2 is a flowchart illustrating a preferred embodiment of a method for distributed probabilistic matrix factorization.

FIG. 2 illustrates an alternate embodiment of a method of practicing the present invention. At step 202, a set of positive drugs shall be selected that are known to have a therapeutic effect of an indication, the indication for which drug repurposing is practiced. For instance, if a model for an indication Multiple myeloma is being built, all drugs which cure the indication Multiple myeloma shall comprise the set of positive drugs. A remaining set of drugs of a universal se of drugs, that form a complementary set to the set of positive drugs maybe referred to as a set of negative drugs.

Further, at step 204, a set of pathways for the set of positive drugs and the set of negative drugs can be listed. At step 206, an action of a drug on each pathway shall be determined. In an event the drug acts on a target on the each pathway a value of one shall be associated with an index value of the pathway, at step 208. However in an event the drug acts on a target on the each pathway, a value of zero can be associated with the index value at step 210. At step 212, a pathway weight can be calculated from the index value of the each pathway. The pathway weight shall be based on a frequency of occurrence of the each pathway in the set of positive drugs and in the set of negative drugs.

In an instance, a binary matrix of the set of positive drugs and the set of negative drugs can be formed. The binary matrix can be a matrix where a first column can consists of the set of pathways and the first row can consists of the set of positive drugs and the set of negative drugs for the indication. Against each pathway, an index value of zero or one can be associated based on whether a drug acts on the each pathway. In an event the drug acts upon the each pathway, the index value can be one. In an event the drug does not act upon the each pathway, the index value can be zero. The binary matrix can be illustrated as below:

|  | Positive drug 1 | Positive drug 2 | Positive drug n | Negative drug 1 | Negative drug n |
|---|---|---|---|---|---|
| Pathway 1 | 1 | 1 | 0 | 0 | 1 |
| Pathway 2 | 0 | 0 | 1 | 1 | 0 |
| Pathway 3 | 1 | 1 | 1 | 0 | 0 |
| ... | 0 | 1 | 1 | 1 | 0 |

A drug score shall be identified for a drug, from the set of negative drugs, based on a pathway weight at step 214. In the disclosed embodiment, the drug score can be calculated as a summation of a product of the pathway weight with the index value of the each pathway. At step 216, a probability score can be calculated from the drug score as a ratio of the drug score and a summation of a set of pathway weights. Based on the probability score of a drug, the drug maybe repurposed at step 218. At step 220, the repurposed drug maybe refined based on a set of predetermined criteria. In the disclosed embodiment, the predetermined set of criteria can include a physiochemical property of the drug, a side effect of the drug, and a QT interval.

Figure 3:
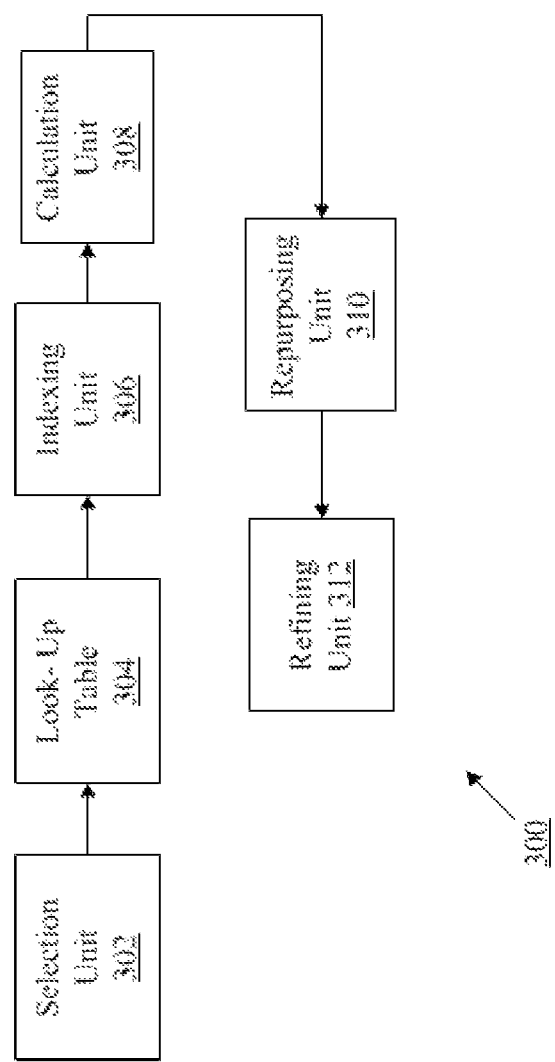
FIG. 3 shows an exemplary system for distributed probabilistic matrix factorization.

FIG. 3 illustrates an exemplary system 300 in which various embodiments of the invention can be practiced. The system comprises of a selection unit 302, a look-up table 304, an indexing unit 306, a calculation unit 308, a repurposing unit 310, and a refining unit 312. The selection unit 302 can select a list of positive drugs for an indication. The set of positive drugs are usually the set of drugs that are known to have a therapeutic effect on said indication. A complementary set of drugs, which are not known to have any effect on the indication, can be referred to as a set of negative drugs. A lookup table 304 can contain a set of pathways for the set of positive drugs and the set of negative drugs. The indexing unit 306 can be configured to associate a pathway for each drug with an index value, based on an action of the each drug on the pathway. The calculation unit 308 can calculate a pathway weight from the index value of the each pathway, based on a frequency of occurrence of the each pathway in the set of positive drugs and in the set of negative drugs. The calculation unit 308 can calculate a drug score for the each drug can be calculated based on the pathway weight. The calculation unit 308 can be further configured to calculate the probability score of the drug as a ratio of the drug score of the drug and a summation of a set of pathway weights, whereby each pathway weight is a positive value. The system can further comprise the repurposing unit 310, configured to suggest a drug for the indication, based on a probability score of the drug. The refining unit 312 can be configured to indicate the repurposed drug for the indication, based on a predetermined set of criteria. The predetermined set of criteria may include one or more of a physiochemical property of the drug, a side effect of the drug, and a QT interval.

Figure 4:
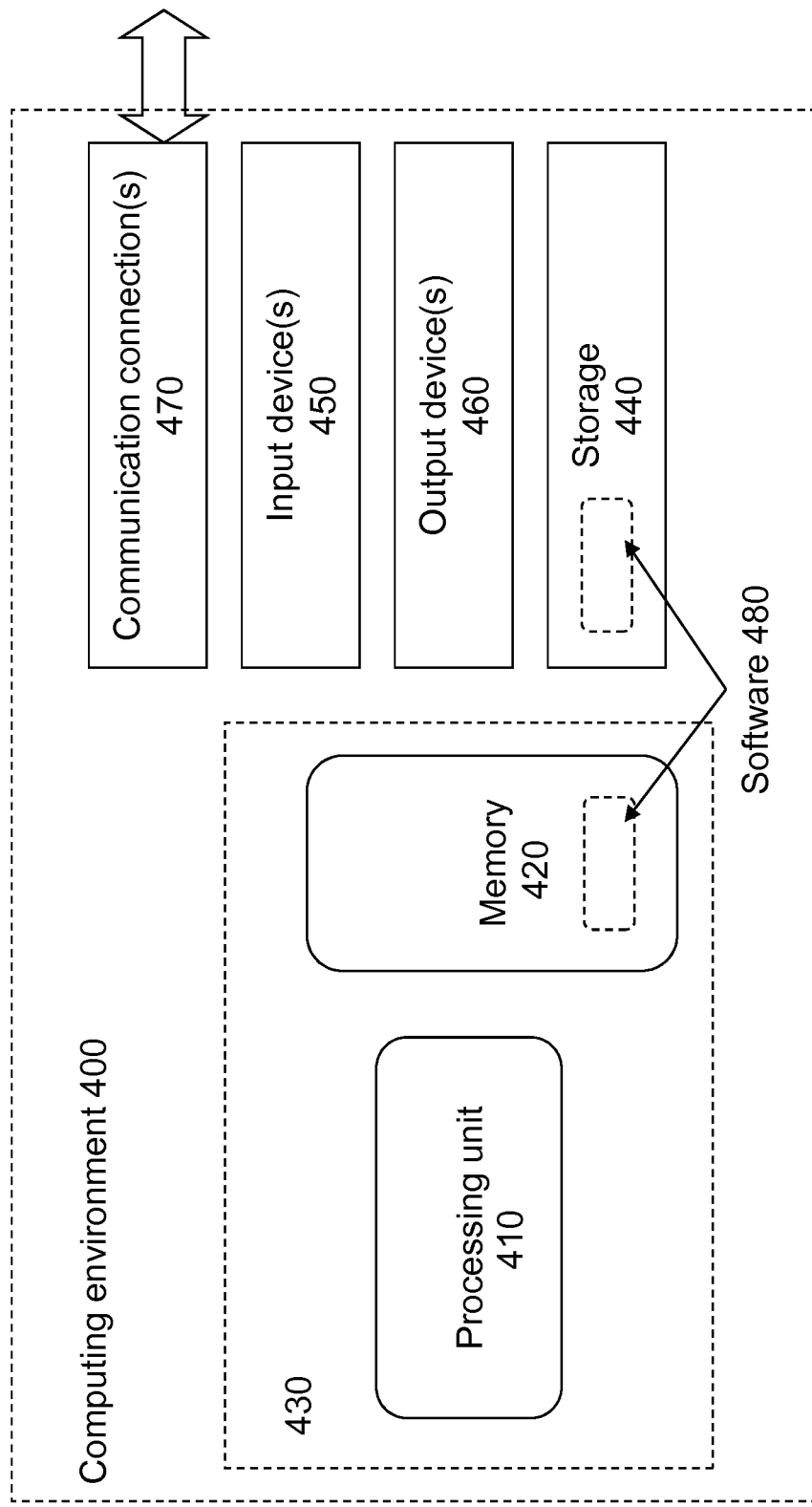
FIG. 4 illustrates a generalized example of a computing environment 400.

One or more of the above-described techniques can be implemented in or involve one or more computer systems. FIG. 4 illustrates a generalized example of a computing environment 400. The computing environment 400 is not intended to suggest any limitation as to scope of use or functionality of described embodiments.

With reference to FIG. 4, the computing environment 400 includes at least one processing unit 410 and memory 420. In FIG. 4, this most basic configuration 430 is included within a dashed line. The processing unit 410 executes computer-executable instructions and may be a real or a virtual processor. In a multi-processing system, multiple processing units execute computer-executable instructions to increase processing power. The memory 420 may be volatile memory (e.g., registers, cache, RAM), non-volatile memory (e.g., ROM, EEPROM, flash memory, etc.), or some combination of the two. In some embodiments, the memory 420 stores software 480 implementing described techniques.

A computing environment may have additional features. For example, the computing environment 400 includes storage 440, one or more input devices 440, one or more output devices 460, and one or more communication connections 470. An interconnection mechanism (not shown) such as a bus, controller, or network interconnects the components of the computing environment 400. Typically, operating system software (not shown) provides an operating environment for other software executing in the computing environment 400, and coordinates activities of the components of the computing environment 400.

The storage 440 may be removable or non-removable, and includes magnetic disks, magnetic tapes or cassettes, CD-ROMs, CD-RWs, DVDs, or any other medium which can be used to store information and which can be accessed within the computing environment 400. In some embodiments, the storage 440 stores instructions for the software 480.

The input device(s) 450 may be a touch input device such as a keyboard, mouse, pen, trackball, touch screen, or game controller, a voice input device, a scanning device, a digital camera, or another device that provides input to the computing environment 400. The output device(s) 460 may be a display, printer, speaker, or another device that provides output from the computing environment 400.

The communication connection(s) 470 enable communication over a communication medium to another computing entity. The communication medium conveys information such as computer-executable instructions, audio or video information, or other data in a modulated data signal. A modulated data signal is a signal that has one or more of its characteristics set or changed in such a manner as to encode information in the signal. By way of example, and not limitation, communication media include wired or wireless techniques implemented with an electrical, optical, RF, infrared, acoustic, or other carrier.

Implementations can be described in the general context of computer-readable media. Computer-readable media are any available media that can be accessed within a computing environment. By way of example, and not limitation, within the computing environment 400, computer-readable media include memory 420, storage 440, communication media, and combinations of any of the above.

Having described and illustrated the principles of our invention with reference to described embodiments, it will be recognized that the described embodiments can be modified in arrangement and detail without departing from such principles. It should be understood that the programs, processes, or methods described herein are not related or limited to any particular type of computing environment, unless indicated otherwise. Various types of general purpose or specialized computing environments may be used with or perform operations in accordance with the teachings described herein. Elements of the described embodiments shown in software may be implemented in hardware and vice versa.

As will be appreciated by those ordinary skilled in the art, the foregoing example, demonstrations, and method steps may be implemented by suitable code on a processor base system, such as general purpose or special purpose computer. It should also be noted that different implementations of the present technique may perform some or all the steps described herein in different orders or substantially concurrently, that is, in parallel. Furthermore, the functions may be implemented in a variety of programming languages. Such code, as will be appreciated by those of ordinary skilled in the art, may be stored or adapted for storage in one or more tangible machine readable media, such as on memory chips, local or remote hard disks, optical disks or other media, which may be accessed by a processor based system to execute the stored code. Note that the tangible media may comprise paper or another suitable medium upon which the instructions are printed. For instance, the instructions may be electronically captured via optical scanning of the paper or other medium, then compiled, interpreted or otherwise processed in a suitable manner if necessary, and then stored in a computer memory.

The following description is presented to enable a person of ordinary skill in the art to make and use the invention and is provided in the context of the requirement for a obtaining a patent. The present description is the best presently-contemplated method for carrying out the present invention. Various modifications to the preferred embodiment will be readily apparent to those skilled in the art and the generic principles of the present invention may be applied to other embodiments, and some features of the present invention may be used without the corresponding use of other features. Accordingly, the present invention is not intended to be limited to the embodiment shown but is to be accorded the widest scope consistent with the principles and features described herein.

While the foregoing has described certain embodiments and the best mode of practicing the invention, it is understood that various implementations, modifications and examples of the subject matter disclosed herein may be made. It is intended by the following claims to cover the various implementations, modifications, and variations that may fall within the scope of the subject matter described.

What is claimed is:

1. A method for drug repurposing, the method comprising:
   selecting, by a drug repurposing computing device, a set of positive drugs for an indication;
   listing, by the drug repurposing computing device, a set of pathways for the set of positive drugs and a set of negative drugs;
   determining, by the drug repurposing computing device, when an action is associated with each of the set of positive drugs and the set of negative drugs acting on each of the pathways;
   associating, by the drug repurposing computing device, each of the pathways for each of the set of positive drugs and the set of negative drugs with a first index value of a plurality of index values, when the determination indicates that an action is associated with each of the set of positive drugs and the set of negative drugs on each of the pathways;
   calculating, by the drug repurposing computing device, a pathway weight for each of the pathways based at least on the first index value of the plurality of index values and on a frequency of occurrence of the each pathway in the set of positive drugs and in the set of negative drugs;
   identifying, by the drug repurposing computing device, a drug score for a drug from the negative set of drugs, based on the pathway weight;
   associating, by the drug repurposing computing device, each of the pathways for of the set of positive drugs and the set of negative drugs with a second index value of the plurality of index values, when the determination indicates that an action is not associated with each of the set of positive drugs and the set of negative drugs on each of the pathways;
   calculating, by the drug repurposing computing device, the pathway weight for each of the pathways based at least on the first index value and the second index value of the plurality of index values and on a frequency of occurrence of the each pathway in the set of positive drugs and in the set of negative drugs;
   calculating, by the drug repurposing computing device, a probability score of the drug as a ratio of the drug score and a summation of a set of pathway weights, whereby each pathway weight is a positive value; and
   repurposing, by the drug repurposing computing device, a drug for the indication, based on the probability score of the drug.

2. The method of claim 1, further comprising:
   refining of the repurposed drug, based on a predetermined set of criteria.

3. The method of claim 2, wherein the first index value is set to one, and the second index value is set to zero.

4. The method of claim 3, wherein the drug score of the each drug is a summation of a product of the pathway weight with the index value of the each pathway.

5. The method of claim 1, wherein the set of negative drugs is a complementary set of the set of positive drugs from a universal set of drugs.

6. The method of claim 1, wherein the set of positive drugs include a plurality of drugs for curing the indication.

7. The method of claim 2, wherein the predetermined set of criteria comprises a physiochemical property of the drug, a side effect of the drug, and a QT interval.

8. A drug repurposing computing device, comprising a processor and a memory coupled to the processor which is configured to be capable of executing programmed instructions comprising and stored in the memory to:

select a set of positive drugs for an indication;

list a set of pathways for the set of positive drugs and a set of negative drugs;

determine when an action is associated with each of the set of positive drugs and the set of negative drugs acting on each of the pathways;

associate each of the pathways for each of the set of positive drugs and the set of negative drugs with a first index value of a plurality of index values, when the determination indicates that an action is associated with each of the set of positive drugs and the set of negative drugs on each of the pathways;

calculate a pathway weight for each of the pathways based at least on the first index value of the plurality of index values and on a frequency of occurrence of the each pathway in the set of positive drugs and in the set of negative drugs; and identify a drug score for a drug from the negative set of drugs, based on the pathway weight;

associate each of the pathways for of the set of positive drugs and the set of negative drugs with a second index value of the plurality of index values, when the determination indicates that an action is not associated with each of the set of positive drugs and the set of negative drugs on each of the pathways;

calculate the pathway weight for each of the pathways based at least on the first index value and the second index value of the plurality of index values and on a frequency of occurrence of the each pathway in the set of positive drugs and in the set of negative drugs;

calculate a probability score of the drug as a ratio of the drug score and a summation of a set of pathway weights, whereby each pathway weight is a positive value; and repurpose a drug for the indication, based on the probability score of the drug.

9. The device of claim 8, wherein the processor coupled to the memory is further configured to be capable of executing at least one additional programmed instruction comprising and stored in the memory to refine the repurposed drug, based on a predetermined set of criteria.

10. The device of claim 9, wherein the first index value is set to one, and the second index value is set to zero.

11. The device of claim 10, wherein the drug score of the each drug is a summation of a product of the pathway weight with the index value of the each pathway.

12. The device of claim 8, wherein the set of negative drugs is a complementary set of the set of positive drugs from a universal set of drugs.

13. The device of claim 8, wherein the set of positive drugs include a plurality of drugs for curing the indication.

14. The device of claim 9, wherein the predetermined set of criteria comprises a physiochemical property of the drug, a side effect of the drug, and a QT interval.

15. A non-transitory computer readable medium having stored thereon instructions for repurposing a drug comprising executable code which when executed by a processor, causes the processor to perform steps comprising:

selecting a set of positive drugs for an indication;

listing a set of pathways for the set of positive drugs and a set of negative drugs;

determining when an action is associated with each of the set of positive drugs and the set of negative drugs acting on each of the pathways;

associating each of the pathways for each of the set of positive drugs and the set of negative drugs with a first index value of a plurality of index values, when the determination indicates that an action is associated with each of the set of positive drugs and the set of negative drugs on each of the pathways;

calculating a pathway weight for each of the pathways based at least on the first index value of the plurality of index values and on a frequency of occurrence of the each pathway in the set of positive drugs and in the set of negative drugs;

identifying a drug score for a drug from the negative set of drugs, based on the pathway weight;

associating each of the pathways for of the set of positive drugs and the set of negative drugs with a second index value of the plurality of index values, when the determination indicates that an action is not associated with each of the set of positive drugs and the set of negative drugs on each of the pathways;

calculating the pathway weight for each of the pathways based at least on the first index value and the second index value of the plurality of index values and on a frequency of occurrence of the each pathway in the set of positive drugs and in the set of negative drugs;

calculating a probability score of the drug as a ratio of the drug score and a summation of a set of pathway weights, whereby each pathway weight is a positive value; and repurposing a drug for the indication, based on the probability score of the drug.

16. The medium of claim 15, further having stored thereon at least one additional instruction that when executed by the processor cause the processor to perform at least one additional step comprising refining of the repurposed drug, based on a predetermined set of criteria.

17. The medium of claim 16, wherein the first index value is set to one, and the second index value is set to zero.

18. The medium of claim 17, wherein the drug score of the each drug is a summation of a product of the pathway weight with the index value of the each pathway.

19. The medium of claim 15, wherein the set of negative drugs is a complementary set of the set of positive drugs from a universal set of drugs.

20. The medium of claim 15, wherein the set of positive drugs include a plurality of drugs for curing the indication.

21. The medium of claim 16, wherein the predetermined set of criteria comprises a physiochemical property of the drug, a side effect of the drug, and a QT interval.

* * * * *